United States Patent [19]

White et al.

[11] 4,032,550
[45] June 28, 1977

[54] PROCESS FOR THE PRODUCTION OF ESTERS

[75] Inventors: John F. White; Jerome C. Bertrand, both of Cincinnati, Ohio

[73] Assignee: Emery Industries, Inc., Cincinnati, Ohio

[22] Filed: Nov. 26, 1975

[21] Appl. No.: 635,468

[52] U.S. Cl. .................. 260/410.6; 260/485 G; 260/485 R; 260/475 P; 260/475 PN; 260/410.9 R; 260/476 R; 260/488 R; 260/488 CD; 260/488 F; 260/487; 260/486 R; 260/486 H; 260/468 R

[51] Int. Cl.² ................... C09F 5/08; C09F 7/10; C11C 3/00

[58] Field of Search .............. 260/410.9 R, 410.6, 260/410.5, 405.5, 468 R, 469, 476 R, 488 R, 488 CD, 488 F, 487, 486 R, 486 H, 485 R, 485 G, 475 P, 475 PN, 410

[56] References Cited

UNITED STATES PATENTS

| | | | |
|---|---|---|---|
| 3,056,818 | 10/1962 | Werber | 260/410.6 |
| 3,677,970 | 7/1972 | Mertzweiller et al. | 252/430 X |
| 3,773,742 | 11/1973 | Kruse | 252/428 X |
| 3,817,931 | 6/1974 | Brooks et al. | 252/428 X |
| 3,840,511 | 10/1974 | Ballard et al. | 252/430 X |

*Primary Examiner*—Winston A. Douglas
*Assistant Examiner*—John F. Niebling
*Attorney, Agent, or Firm*—Gerald A. Baracka; John D. Rice

[57] ABSTRACT

Ester products are obtained using an immobilized supported transition metal catalyst. Esters and polyesters having improved color and containing virtually no residual metal catalyst can be obtained with this process either by direct esterification or by ester interchange.

12 Claims, No Drawings

PROCESS FOR THE PRODUCTION OF ESTERS

BACKGROUND OF THE INVENTION

A variety of procedures are available for the production of simple and polymeric ester products. These include direct synthesis by reacting an organic alcohol and carboxylic acid, and interchange reactions where an acyl

moiety or alkoxyl (—OR) moiety of an existing ester is exchanged for a different acyl or alkoxyl moiety (see Kirk-Othmer "Encyclopedia of Chemical Technology" Volume 8, pages 356–365, John Wiley & Sons, New York, 1965). Such reactions include acidolysis (reaction of the ester with a carboxylic acid to exchange acyl moieties) and alcoholysis (reaction of the ester with an alcohol to exchange alkoxyl moieties). In transesterification reactions, two ester products are heated to bring about interchange of both the acyl and alkoxyl groups as follows:

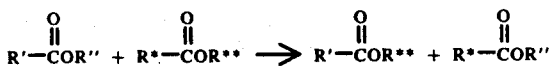

The ester interchange reactions are particularly useful in situations where one of the resulting products is relatively low boiling and can be removed by distillation to shift the equilibrium and drive the reaction to completion. In the preparation of polyesters, for example, this feature makes it possible to obtain high molecular weight polymers. By causing the redistribution of the acyl moieties it is also possible to modify triglycerides or similar compounds containing a plurality of ester groups to obtain a wide variety of useful products.

With the above procedures it is generally advantageous to employ catalysts. Mineral acids such as hydrochloric acid, sulfuric acid and phosphoric acid have been generally used for esterification as have other acids, such as p-toluenesulfonic acid and benzenesulfonic acid. Basic materials, notably the alkali metal alkoxides and alkali and alkaline earth metal carbonates have also been used in ester production as catalysts for alcoholysis reactions. There are, however, two major problems associated with the use of these acidic and basic catalysts — they promote side reactions resulting in the formation of undesirable by-products and require neutralization at the completion of the reaction.

Because of these drawbacks transition metal compounds, particularly titanium compounds containing alkoxyl or acyl groups have found increasing use as catalysts for ester processes since they do not require neutralization and they minimize objectionable side reactions. It is well documented, however, that these titanium catalysts hydrolyze in the presence of water with proportionate loss of activity. This feature limits their utility and in many cases requires a large amount of catalyst to insure completion of the esterification. This adds increased cost to process and, more importantly, makes it increasingly difficult to obtain esters free of catalyst residues. The presence of catalyst residue in the ester product is undesirable since it imparts undesirable haze or color to the ester and contributes to the oxidative, thermal and hydrolytic instability of the ester.

Condensed polytitanates of varying degrees of hydrolysis and polymeric orthotitanates derived from organic polyhydroxy compounds have been disclosed in U.S. Pat. No. 2,689,858 and German Pat. No. 1,142,868, respectively. These catalysts present a definite improvement in hydrolytic stability over alkyl orthotitanates and titanium acylates, however, the amount of catalyst residue in the ester products is still unacceptable, particularly for critical applications where sparkling clear ester products with good stability are required.

SUMMARY OF THE INVENTION

We have now discovered a process for the preparation of ester products which virtually eliminates the problems generally associated with ester production. The present process is adaptable to batch, semi-continuous or continuous operations whereby ester products, including both simple esters and polyesters, are obtained either by direct esterification or by any of the known interchange type reactions. Due to the hydrolytic stability of the catalyst used, the process can be used for ester reactions where water is formed as a by-product. Furthermore, with the process of this invention undesirable side reactions are virtually eliminated and acceptable rates of reactions are obtained employing small amounts of catalyst. Because of the small amount of catalyst required and the fact that the catalyst is immobilized on a support and exhibits exceptional hydrolytic stability, it is possible to obtain extremely useful ester products containing very low levels, and in many cases negligible amounts, of catalyst residue. As a result ester products which are virtually colorless (water-white) and exhibit good stability upon subsequent storage and use can be obtained.

Still another useful feature of this process which is extremely important in batch production is the fact that the heterogeneous catalysts are readily separable from the resulting ester products by filtration and are reuseable. Another feature which is quite unexpected and an important consideration for commercial operations is the adaptability of the process for use with impure acid, anhydride, alcohol or ester feeds which typically contain ketonic, aldehydic and olefinic functional groups and do not require costly and time consuming purification prior to use. Such impurities normally interfere with the ester production and/or result in highly colored products which are unacceptable for all but the lowest quality applications. With our process, however, it has been found that these low grade feeds can be used directly and the resulting products have improved color and stability.

The present process comprises heating the reactants in a liquid state at an elevated temperature in the presence of a heterogeneous transition metal catalyst. Temperatures can range from about 100° C to 300° C and the process can be carried out at atmospheric or reduced pressure. The process is adaptable to batch, continuous or semi-continuous operations for the production of esters and polyesters by either direct esterification or ester interchange. Aliphatic, aromatic and alicyclic mono- and polyfunctional acids and alcohols can be used in the process. The process is also useful for ester interchange with both synthetic and naturally occurring (e.g. triglycerides) ester products. An immobilized supported transition metal (Group IVb, Vb and VIb) catalyst is used and preferably the transition metals are titanium, zirconium, hafnium or vanadium. These catalysts are obtained by the reaction of a molar excess transition metal alkoxide with a hydroxylic support, preferably alumina, silica or mixtures thereof, at an elevated temperature with agitation in a hydrocarbon medium and in the presence of water. The catalysts will contain about 3 to 60 weight percent transition metal which is present on and bound to the support by bridging oxygen linkages (—O—) as a rigid polymeric cross-linked network of transition metal atoms bonded to each other through oxygen linkages. The amount of the supported catalyst used for the ester process can be as low as 0.0005 weight percent based on the reactants charged and can range to very large amounts such as where the reactants are passed through a heated column packed with the catalyst.

DETAILED DESCRIPTION

The present invention relates to the batch, continuous or semi-continuous production of ester products, including both simple esters and polyesters. It is adaptable for use with those reactions where a carboxylic acid or carboxylic acid anhydride is directly combined with a mono- or polyfunctional alcohol to yield an ester. It is similarly useful with any of the known ester exchange-type reactions whereby an acyl and/or alkoxyl radical from an existing ester is interchanged with another acyl and/or alkoxyl radical. As indicated, the process is useful for the formation of simple ester products where at least one of the reactants (acid, anhydride or alcohol) is monofunctional; however, the simple ester can contain more than one ester moiety within the molecule such as where glycerol is reacted with a fatty acid. The process also finds use for the preparation of polyesters, that is, polymeric materials containing a repeating ester moiety.

The process is useful with any mono- or polycarboxylic acid or anhydride including aliphatic, aromatic, or alicyclic acids or mixtures thereof which can additionally contain other substituents. The acids may be saturated or contain olefinic unsaturation. Representative acids include acetic, vinyl acetic, phenylacetic, triphenylacetic, propionic, acrylic, methacrylic, $\beta$-phenylacrylic, n-butyric, isobutyric, valeric, isovaleric, 5-phenyl-n-valeric, hexoic, 2-ethylhexoic, heptoic, caproic, octanoic, pelargonic, lauric, myristic, palmitic, stearic, oleic, erucic, linoleic, linolenic, eleostearic, lignoceric, malonic, succinic, glutaric, adipic, pimelic, azelaic, sebacic, decane-1,10-dicarboxylic, pentadecane-1,15-dicarboxylic, pentacosane-1,25-dicarboxylic, 1,2,3-propane tricarboxylic, crotonic, maleic, fumaric, mesaconic, citraconic, itaconic, muconic, aconitic, and the like.

Useful alicyclic acids included are cyclopropane carboxylic, cyclobutane carboxylic, cyclopentane carboxylic, cycloheptane carboxylic, cyclohexane carboxylic, cyclopropane dicarboxylic, cyclohexane dicarboxylic, cyclohexane-1,2,3,4,5,6-hexacarboxylic, cyclopentene-2-carboxylic, 1-cyclohexene-1-carboxylic, cyclohexadiene-1,2-dicarboxylic, 1,3-cyclohexadiene-1,4-dicarboxylic, the dicarboxylic acid formed by the Diels-Alder addition of acrylic acid to linoleic acid, and the like.

Suitable aromatic acids for use in the present process include benzoic, the toluic acids, alpha-naphthoic, beta-naphthoic, o—, m— and p-ethyl benzoic, p-phenyl benzoic, phthalic, isophthalic, terephthalic, trimellitic, pyromellitic and the like.

Numerous substituted acids can be used including hydroacetic, chloracetic, bromoacetic, cyanoacetic, lactic, alpha- or beta-hydroxypropionic, citric, ricinoleic, alpha- or beta-chloroacrylic, beta-bromoacrylic, 2-hydroxycyclohexane carboxylic, o—, m— and p-chloro or bromobenzoic o—, m— and p-hydroxybenzoic, o—, m— and p-nitrobenzoic, o—, m— and p-methoxybenzoic, hydroxyphthalic and the like. Various mixed acids obtained from numerous natural sources such as tall oil fatty acids, lanolin fatty acids, coconut fatty acids and montan wax acids or the like can also be used. High molecular weight acids including dimer, trimer and higher polymer acids obtained by the polymerization of olefinically unsaturated fatty acids, such as oleic acid, linoleic acid or mixtures thereof, are also useful as are other high molecular weight acid products such as the $\alpha$-alkyl or $\alpha,\alpha$-dialkyl branched acids, obtained by the free radical addition of short-chain monobasic acids, e.g. propionic acids, to high molecular weight $\alpha$-olefins, and high molecular weight mixed acid products obtainable by ozonization or oxidation of high molecular weight olefins. Typical anhydrides of mono- and dibasic acids which can be used for the process include acetic anhydride, adipic anhydride, maleic anhydride, phthalic anhydride, trimellitic anhydride, benzoic anhydride, or the like.

Alcohols which can be reacted with the aforementioned carboxylic acids and anhydrides are monoalcohols or di-, tri- or higher polyfunctional alcohols. They include aliphatic, alicyclic and aromatic alcohols, which may contain additional substituents, and ether alcohols i.e. intermolecular ethers formed by the condensation of two or more molecules of a polyol accompanied by the elimination of water. By way of illustration, useful monohydric alcohols include ethanol, chloroethanol, cyanoethanol, n-proponal, sec-propanol, n-butanol, t-butanol, isoamyl alcohol, n-hexanol, 2-ethylhexanol, n-octanol, n-decanol, isodecanol, capryl alcohol, lauryl alcohol, myristyl alcohol, cetyl alcohol, stearyl alcohol, oleyl alcohol, oxo alcohols such as tridecyl alcohol which is mainly tetramethyl-1-nonanol and hexadecyl alcohol which is a complex mixture of primary alcohols characterized as 2,2-dialkyl ethanols where the alkyl groups are predominantly methyl-branched $C_6$ and $C_8$ radicals, cyclohexanol, benzyl alcohol, o—, m— and p-methoxybenzyl alcohol, o—, m— and p-methylbenzyl alcohols, phenylethyl alcohol, triphenylethyl alcohol, and the like. Useful polyols for this invention include ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like. Ether alcohols which can be employed are diethylene glycol, triethylene glycol, tetraethylene glycol, polyoxyethylene or polyoxypropylene glycols of molecular weight up to about 4000, diethylene glycol monomethylether, diethylene glycol monoethylether, triethylene glycol monomethylether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and the like.

In addition to the acids, anhydrides and alcohols mentioned above the esters formed therefrom can also be used in the process. The esters can be used in exchange reactions including acidolysis, alcoholysis and transesterification. Both synthetic esters and ester products derived from natural sources are useful for this purpose. While typically the ester contents of such naturally occurring products will be quite high, products containing less than 50% ester compounds are also useful. Naturally occurring fats and oils derived from both animal and vegetable sources are advantageously used in the process of this invention and can be modified in many ways to obtain useful ester products. While these fats and oils are comprised primarily of triglycerides other esters can also be present.

The reaction conditions employed in this process can vary over a wide range depending on the type of reaction involved, the particular reactants and the results to be obtained. In general, temperatures will range between about 100° and 300° C and, more generally, from about 125° to 250° C. Reactions conducted at temperatures much below 100° C do not proceed at an acceptable rate and no advantage is generally served by operating at temperatures much above 300° C. The temperature and other reaction conditions will, of course, depend upon the method of conducting the process which as already mentioned can be either a batch, continuous or semi-continuous operation. It will be evident that in a continuous operation, for example, where a column is packed with the catalyst in suitable form and where very short contact times are obtained, temperatures will generally be higher than might be required for a batch system. Also, it is evident that in an operation where the product proceeds through a series of reaction vessels, it may be advantageous to operate the finishing reactors at higher vacuum and/or temperatures. Numerous process variations are contemplated and are within the scope of this invention.

The reaction can be conducted at atmospheric pressures or the pressure may be reduced or increased above atmospheric. In general, the same criteria as mentioned above for temperature will apply to the pressure requirements of the system. To facilitate completion of reaction by removing water or other volatile products, e.g. glycols, the final stages of the reaction will generally be conducted at reduced pressure. These procedures are particularly advantageous where ester products having low acid values are desired and where formation of polyesters of high molecular weight are required.

It is not necessary that the process be conducted in an inert solvent or inert diluent as long as the reactants remain liquid. It may be advantageous, however, to employ a solvent or diluent to facilitate handling of the reactants or contact of the reactants with the catalyst in order to achieve a more uniform rate of reaction. The particular solvent or diluent employed is not critical so long as it does not react with the reactants or catalyst or otherwise interfere with the reaction. Hydrocarbon solvents, both aliphatic and aromatic, are particularly useful for this purpose. Especially useful are those hydrocarbons which form an azeotrope with water that is lower boiling than any of the reaction components so that any water formed can be azeotropically removed from the reaction mixture thus driving the reaction to completion.

The time of reaction will vary widely depending on the aforementioned variables, however, it generally has been found that even in batch type operations extremely rapid rates of reaction are obtained with the present process so that essentially complete conversion is obtained within several hours.

For the present process a supported transition metal catalyst containing from about 3 to about 60 percent by weight of a Group IVb, Vb or VIb metal bound to the support is used. The groups referred to herein are from the Periodic Table of Elements as set forth on the inside cover of the Handbook of Chemistry and Physics, 56th ed. (1975–76), CRC Press, Cleveland, Ohio. The catalysts are obtained by reacting a hydroxylic support with a molar excess of a transition metal alkoxide in an inert hydrocarbon and in the presence of water. As a result of the reaction of the transition metal alkoxide and oligomers thereof with the hydroxyl groups of the support, the immobilized catalyst has a complex structure consisting of a highly cross-linked transition metal-containing polymeric network bound to the surface through bridging oxygen (—O—) linkages. The polymeric network is a cross-linked matrix of transition metal atoms bonded to each other by bridging oxygen (—O—) linkages resulting from polycondensation of the transition metal alkoxide. These catalysts, while necessarily prepared in the presence of water, still contain sufficient unreacted alkoxide groups to have a high degree of catalytic activity. The alkoxide groups are present on the surface of the transition metal polymer and may also be present within the rigid polymeric matrix. Particularly useful transition metal catalysts for this invention are those obtained with titanium, zirconium, hafnium and vanadium and contain from about 5 to 50 weight percent of the transition metal bound to the support. Supported catalysts wherein the transition metal is titanium are especially useful for the present process and form a preferred embodiment of this invention.

To obtain the catalysts useful for this process a transition metal alkoxide is reacted with a hydroxylic support. The transition metal alkoxide also undergoes condensation to form a polymeric network which is bound to the support matrix. Useful transition metal alkoxides have the general formula $$M(OR)_nQ_m$$

where M is a transition metal selected from Groups IVb, Vb and VIb, OR is an alkoxy radical containing 1 to 18 carbon atoms, such as ethoxy, n-propoxy, isopropoxy, n-butoxy, isobutoxy, tert-butoxy, n-octoxy, 2-ethylhexyloxy, n-decyloxy, allyloxy, tridecyloxy, stearyloxy, isotridecyloxy, cyclopentyloxy, cyclohexyloxy and the like, n is an integer from 2 up to the valence of the metal M, Q is an inert group which does not react with the hydroxyl groups of the support, an alkoxide radical OR or alcohol (ROH) formed therefrom, and m is an integer so that $n + m$ satisfies the valence of the transition metal M. Especially useful transition metal alkoxides are those where the transition metal is titanium, zirconium, hafnium or vanadium and the alkoxy radical is a saturated branched or straight-chain radical containing 2 to 8 carbon atoms. Illustrative transition metal alkoxides include, for example, tetraethoxy titanium, tetraisopropoxy titanium, tetrabutoxy titanium, tetraisobutoxy titanium, tetrabutoxy zirconium, tetraisopropoxy zirconium, pentaisopropoxy vanadium, triisopropyl vanadate, tributyl vanadate, tetraisopropoxy hafnium, chromium (II)

isopropoxide, chromium (IV) isoproxide. Particularly useful transition metal alkoxides for the preparation of the supported catalysts have all their available valences satisfied with a saturated alkoxide radical. Titanium tetraalkoxides are especially useful because of their availability, reactivity with the support and the superior catalysts formed therewith.

The transition metal alkoxides can be reacted with any of the conventional and commonly used support materials having a hydroxylic surface, that is, containing a plurality of hydroxylic groups attached to the surface of the matrix, to obtain the supported catalysts. The surface hydroxyl groups provide sites for attachment of the transition metal alkoxide and oligomers thereof. The supports can be either synthetically produced or naturally occurring materials and can be anhydrous or contain adsorbed water. There is no particular restriction with regard to the physical form of the support, and while they are generally in finely-divided particulate form, the support may also be in the form of granular particles, spheres, hollow tubes, rings, rods, fibers, platelets or the like.

The type of supports used can be widely varied, the only requirement being that the surface contain hydroxyl groups to permit reaction with the transition metal alkoxide. Neither is the hydroxyl content of the support critical for this invention and supports containing a small amount of hydroxyl functionality on the surface, such as the diatomaceous earths, as well as those supports which have very high numbers of hydroxyl groups can be employed. To illustrate the wide variety of support materials which can be employed the following partial list is provided and includes channel carbon blacks, furnace carbon blacks, alumina, silica, fumed silica, silica gel, naturally occurring clays such as the kaolinite types, the smectite types particularly montmorillonite clay, the vermiculite types, the palygorskite types, the chlorite and mica types and the like, zeolites, zirconia, titania, thoria, magnesia, aluminates such as bauxite and corundum, silicates such as chrysotile and actinolite and the like. Support materials of silica and alumina or mixtures thereof, which can be either naturally occurring or synthetically produced, and which can also contain small amounts of alkali and alkaline earth oxides, iron oxide, zinc oxide and the like, are especially useful supports for the preparation of catalysts of this invention. The support materials may be used as such or they may be further activated, such as by acid treatment or the like, prior to the reaction with the transition metal alkoxide.

To obtain these catalysts an excess of the transition metal and the hydroxylic support are heated with agitation at a temperature between about 100° and 300° C in an inert hydrocarbon medium and in the presence of water. More preferably, the reaction temperature will be in the range 120°-250° C. The reaction may be conducted at atmospheric pressure or pressures up to about 1000 psig and, more preferably, up to about 500 psig.

The inert hydrocarbon will typically consist of an inert liquid aliphatic hydrocarbon which can also contain some unsaturated and aromatic materials. It is generally desirable, however, to employ hydrocarbons which are predominantly saturated since the presence of olefinic unsaturation can result in undesirable color formation. The aliphatic saturated hydrocarbons will typically be oily liquids which are mixtures of hydrocarbons in the range $C_{14-32}$ having a boiling point greater than 140° C. Useful aliphatic hydrocarbons include such materials as liquid petrolatum, liquid paraffin and preferably the numerous commercially available mineral oils and mineral seal oils. The weight ratio of the hydrocarbon to the support will generally range from about 0.5:1 to 40:1 and, more preferably, be between 2:1 and 25:1. As previously indicated, an excess of the transition metal alkoxide (based on the available hydroxyl groups of the support) is required. The ratio of transition metal alkoxide molecules per available hydroxyl groups will be greater than 1:1 and may range up to about $10^6$:1 and, more preferably, will be between about 1.5:1 and $10^4$:1. With supports having relatively high hydroxyl contents, e.g. $10^{-4}$ and $10^{-3}$ equivalents hydroxyl functionality per gram support, this ratio will usually range from about 2:1 to $10^2$:1.

As previously indicated the presence of water is essential to obtain these supported catalysts. Where the reaction is conducted under anhydrous or essentially anhydrous conditions condensation of the transition metal alkoxide forming the rigid transition metal-containing polymer will not occur. The amount of water required will vary depending on the amount of transition metal alkoxide charged and the extent of condensation and cross-linking desired. It can be stated as a general rule, however, that one molecule water is required for each —O— linkage to be formed (excluding the —O— linkage to the support). The presence of larger amounts of water, even as high as a ten-fold molar excess, does not, however, detract from the reaction or the activity of the resulting catalysts.

The water may be added at the outset of the reaction, charged continuously or intermittently throughout the reaction, or formed in situ. In a typical reaction procedure for the preparation of the catalyst, a portion of the required water is charged at the outset of the reaction and the remainder generated in situ as the reaction progresses by dehydration of alcohols which are formed as by-products. When the water is added at the outset, it may be added as such or adsorbed on the support. This latter approach has been found to be an especially convenient way to introduce water into the system. It is also believed that the presence of water at the surface of the support promotes the condensation reaction. In a preferred method for obtaining the catalyst all or a portion of the required water is generated in situ by the dehydration of by-product alcohols. A small amount of acid, such as sulfuric acid, may be added but is not necessary to facilitate the dehydration. For additional details with regard to the catalyst preparation reference may be had to our copending application Ser. No. 635,467, filed of even date herewith and entitled SUPPORTED TRANSITION METAL CATALYSTS AND IMPROVED PROCESS FOR THEIR PREPARATION, which is incorporated herein by references being made thereto.

Because of the superior activity of the immobilized catalysts very small amounts may be used and acceptable reaction rates obtained. However, since the transition metal is bound to the support the use of large amounts of catalysts is not detrimental and virtually all of the catalyst residue can be removed from the ester product at the completion of the reaction using simple filtering procedures. The catalysts used may range from about as low as 0.0005 weight percent up to very large amounts since it is possible to produce ester products continuously by passing the reactants through a column packed with the supported transition metal catalyst.

More usually, however the catalysts will be present in an amount from about 0.001 percent up to about 10 weight percent based on the total reactants charged. In typical batch and semi-continuous operations, for the production of both esters and polyesters by either direct esterification or ester interchange, catalyst amounts from 0.01% to 1% by weight are usually employed.

The advantages of the present process which utilizes immobilized transition metal catalysts are numerous. Because the active metal catalyst is bound to the support and not dissolved in the reaction mixture, metal-containing color bodies formed are trapped on the surface of the heterogeneous catalyst and can be removed by filtration at the end of the reaction. For this reason, ester and polyester products by this process generally have improved color as compared to ester products made using homogeneous catalysts. This feature also makes the process useful with reactants containing ketonic, aldehydic and olefinic impurities such as might be obtained from commercial operations, without the need for costly and time consuming prior purification.

Another important advantage of this process is the fact that virtually all the catalyst can be removed at the end of the reaction using simple filtration procedures. It is not uncommon for esters and polyesters containing less than 1 ppm titanium to be obtained and the resulting metal-free esters or polyesters accordingly have increased hydrolytic, oxidative and thermal stability as compared to ester products obtained using the heretofore known catalysts. This feature also makes it commercially feasible to produce ester products useful in certain applications where it was previously not possible or was impractical to lower the residual metal content to acceptable levels. Such applications include food and other critical applications where esters and polyesters are employed, such as plasticizers for PVC or other polymers used for food wrap, blood bags, etc. It is also possible with this process to obtain three centistoke (210° F) and one centistoke (500° F) ester turbine lubricants which meet and surpass the rigid specifications of MIL-L-7808G and MIL-L-27402 with regard to metal content.

Still other advantages are possible such as in the production of hydroxyl-terminated polyesters useful as polymer intermediates for reaction with diisocyanates to obtain flexible polyurethanes. In the presence of residual metal catalysts, undesirable by-product formation (e.g. biurets, ureas and allophanes) is obtained which results in cross-linking and detracts from the flexiblity of the polyurethane.

These and other advantages will be evident from the following examples which illustrate the invention more fully. In these examples all parts and percentages are on a weight basis unless otherwise indicated.

EXAMPLE I

A supported titanium catalyst was prepared in a jacketed stainless steel reactor equipped with an agitator, thermocouple and condenser with a receiver. The reactor was charged with 90 parts mineral oil (White Oil No. 70) and 10 parts of a naturally acidic montmorillonite clay containing about 4% adsorbed water. Heating and agitation were commenced and subsurface addition of a solution of 33.5 parts tetraisopropyl titanate (Tyzor TPT manufactured by E. I. duPont de Nemours and Company) in 27.5 parts mineral oil begun. The addition was continued for 1¼ hours during which time the reaction temperature was increased to 110° C. When the temperature reached 120° C a second addition of a solution of 21 parts mineral oil and 34 parts tetraisopropyl titanate was begun. When the temperature reached 140° C distillate (isopropanol) began to collect. By the time the temperature reached 170° C and the second addition was complete (addition time 1¼ hours), the rate of distillate recovery had increased significantly. Heating was continued and the temperature increased to about 200°–210° C and maintained for an additional five hours while collecting isopropanol and venting propene and any other volatile products which did not condense. Some foaming was noted; however, it did not interfere with the reaction or collection of the distillate. After cooling to about 70° C the supported catalyst was collected on a filter, washed several times with isopropanol until the filtrate was clear and air-dried. There was a 205% increase in weight of the support. Analysis (atomic absorption) showed the product contained 37.8 weight percent titanium. The supported catalyst was a free-flowing grayish powder which was almost fluid in appearance.

To demonstrate the utility of the above catalyst a reaction was carried out where esterification and ester interchange occurred simultaneously to produce an emulsifiable ester lubricant. 228 Grams (1.0 equivalent) refined palm oil, 60 grams (0.3 equivalent) polyoxyethylene glycol having an average molecular weight of 400 and 85.8 grams (0.3 equivalent) EMPOL 1014 Dimer Acid containing 95% $C_{36}$ dibasic acid were charged to a reactor with 0.01 weight percent (based on the total reactant charge) of the immobilized titanium catalyst and the reaction mixture heated to 220° C for about five hours while removing water. After cooling, the mixed ester product was filtered using a 0.5 weight percent diatomaceous earth filtering aid. The final mixed ester product (acid value 1.6) had good thermal stability and lubricating properties and was readily emulsifiable in cold water. The ester product was a useful industrial lubricant for metal working applications.

EXAMPLE II

To further demonstrate the utility of this invention a hydroxyl-terminated polyester useful in the preparation of flexible urethane polymers was prepared by reacting 364 parts 1,4-butanediol and 1076 parts EMPOL 1010 Dimer Acid (97% $C_{36}$ dibasic acid and 3% $C_{54}$ tribasic acid). The reaction mixture was heated with 0.05 parts 50% $H_3PO_2$ solution to 225° C while pulling a vacuum on the system to facilitate water removal. When the acid value reached about 2, 1 part of the catalyst of Example I was added to the reaction mixture and the vacuum increased to about 5 Torr and the temperature maintained for about 30 minutes until distillate collection was complete. The resulting polyester product has excellent clarity and color and contained 2.4 ppm titanium. The hydroxyl-terminated polyester was readily reacted with diisocyanate to obtain a useful flexible polyurethane product.

EXAMPLE III

The supported titanium catalyst of Example I was also used to promote the exchange reaction (alcoholysis) between the methyl esters of short-chain dibasic acids and an "oxo" alcohol. For the reaction, 2585 grams tridecyl alcohol and 915 grams dimethyl esters of mixed dibasic acids (predominantly glutaric and succinic) were charged to an esterification reactor with 3.5 grams activated carbon, 0.70 grams 50% $H_3PO_2$ and 0.35 grams of the immobilized supported titanium catalyst. The reaction mixture was agitated with heating. Methanol collection began at about 180° C and at 225° C when the rate of collection was almost negligible a vacuum was pulled on the system. Excess tridecyl alcohol was then distilled from the reaction mixture by increasing the vacuum to 3 Torr. The final ester product, after filtration had an acid value of 0.1, hydroxyl value of 1.2 and contained 94% of the diester of tridecyl alcohol. The ester contained only 0.6 ppm residual titanium and had excellent color, 96/98, as determined by percent transmittance (%T) at 440 and 550 millimicrons by spectrophotometric analysis.

EXAMPLE IV

Triethylene glycol (413 grams; 5.5 equivalents) and heptanoic acid (787 grams; 6.05 equivalents) were reacted by heating the mixture up to 225° C in the presence of 0.12 grams of the supported catalyst of Example I while removing the by-product water formed. The pressure was reduced during the latter stages of the reaction to facilitate water removal. After essentially all the water was removed (6 hours) the reaction mixture was cooled to 100° C and high vacuum (2–5 Torr) applied while reheating to 200° C over a 50 minute period. The diester had an acid value of 0.1, hydroxyl value of 11.8, 100° F viscosity of 82 centistokes and contained less than 0.5 ppm residual titanium with a color (%T) of 100/100.

Similar esterifications were conducted using the catalyst of Example I. When 2-ethylhexanol and phthalic anhydride were reacted the diester product contained less than 1 ppm titanium and had excellent color. The esterification product of 1,3-butylene glycol and pelargonic acid also contained less than 1 ppm titanium.

EXAMPLE V

A polyester was prepared by heating (225° C) 595 grams adipic acid, 449 grams propylene glycol, 39 grams pelargonic acid and 217 grams of mixed mono- and dibasic (75:25) acids with 0.13 grams $H_3PO_2$ while removing water. When the acid value was decreased to about 20, 0.13 gram of the catalyst of Example I was added to the reaction mixture. A low vacuum was applied to facilitate the removal of water which is necessary to complete the esterification. When the theoretical amount of water had been collected a high vacuum (3 Torr) was applied to effect ester interchange and transesterification by removal of volatile products. After filtering the final polyester product had a 100° F viscosity of 1017 centistokes and contained 0.7 ppm residual titanium.

EXAMPLE VI

802 Grams adipic acid, 813 grams phthalic anhydride, 695 grams propylene glycol and 1190 grams 2-ethylhexanol were charged and reacted in accordance with the procedure of Example V. The final filtered polyester product (residual titanium content 0.7 ppm) had an acid value of 0.3 and 100° F kinematic viscosity of 531 centistokes.

EXAMPLE VII

A mixed ester base stock was obtained by esterifying azelaic acid, phthalic anhydride and mixed saturated aliphatic mono- and dibasic acids (75:25) with excess propylene glycol (0.625:0.222:0.150:1.25 equivalents ratio of the respective reactants). The mixed acids used are ozonization by-product acids containing sizeable amounts of olefinic impurities which typically result in highly colored ester products. The reactants were heated up to 230° C for about nine hours in the absence of catalyst while removing water. The resulting mixed ester product had an acid value of 5.4, 100° F kinematic viscosity of 430 centistokes and the color (%T) was 35/82. This "base stock" was used to demonstrate the advantages of the present process as follows:

A polymeric orthotitanic acid ester catalyst similar to the heterogeneous catalysts of German Pat. No. 1,142,868 was prepared from ethylene glycol and tetrabutyl titanate. To prepare the catalyst, 62 grams polymer grade ethylene glycol (dried prior to use) and 83.6 grams tetrabutyl titanate were reacted by heating at about 130°–150° C. Within a very short time a white suspension formed and 30 mls butanol were collected. After cooling the reaction mixture was filtered and the catalyst washed with hot xylene and dried in a vacuum oven at 110° C. This heterogeneous polymeric catalyst (VIIa) contained 35.5 weight percent titanium.

An immobilized supported catalyst was prepared by reacting 60.9 parts tetraisopropyl titanate and 10.8 parts of an acidic montmorillonite clay in 125 parts 70 SUS mineral oil at a temperature up to 170° C for 3 hours while collecting isopropanol and propene. After cooling the reaction mixture was filtered and the catalyst washed with isopropanol until the filtrate was clear. After air-drying a 209 weight percent increase of the support $$\left( \frac{\text{Final Wt.} - \text{Initial Wt.}}{\text{Initial Wt.}} \times 100 \right)$$

was obtained. The catalyst (VIIb) contained 32.6 weight percent bound titanium.

To demonstrate the superior results obtained with the immobilized catalysts of this invention two reactions were conducted wherein 1000 grams of the above-prepared base stock was combined with 0.031 weight percent catalyst VIIa and 0.057 weight percent catalyst VIIb. Both reaction mixtures were heated at 225° C under high vacuum (1–2 mm Hg) for two hours while stripping glycol. The catalysts were removed by filtration and the polyesters analyzed for titanium residue and color. While both polyester products showed a significant increase in viscosity and had acid values 0.5 the product obtained with catalyst VIIa had very poor color (% T = 4/48) and contained 86 ppm residual titanium. The polyester prepared using the immobilized catalyst of this invention (VIIb) had much improved color (% T = 19/75) and contained 2.4 ppm titanium.

EXAMPLE VIII

To demonstrate the ability of the supported catalysts to be recycled for additional use, an immobilized catalyst was prepared using preformed spheres (4–5 mm) of an acidic montmorillonite clay. 10.7 Grams of the clay spheres and 11.1 grams tetraisopropyl titanate were combined in 200 grams mineral oil and heated to 200° C over a three hour period while collecting byproduct isopropanol and propene. The dried support weighed 15.3 grams and contained about 10 weight percent titanium.

The above catalyst (10 grams) and 1000 grams of the base stock of Example VII were combined and heated at 225° C under high pressure for exactly 2 hours to effect polyesterification. The product was cooled at 190° C, filtered and the catalyst spheres recovered and reused with another 1000 grams of the base stock under identical reaction conditions. The results obtained for the polyester products from the two runs were as follows:

|  | POLYESTER OF: | |
|---|---|---|
|  | 1st run | 2nd run |
| Acid Value | 0.4 | 0.2 |
| Hydroxl Value | 16.8 | 16.9 |
| 100° F Kinematic Viscosity (centistokes) | 1351 | 1407 |

EXAMPLE IX

To further demonstrate the versatility of the present process and the superior results obtained using the immobilized catalyst this comparative example is presented.

For comparison with the immobilized titanium catalyst of Example I, a heterogeneous catalyst was prepared from tetraisopropyl titanate and the acidic montmorillonite clay in accordance with the teachings of Brooks et al U.S. Pat. No. 3,817,931. The reaction was conducted under anhydrous conditions. The clay (9.69 grams) calcined under nitrogen for 2 hours at 350° C to remove water was charged to a reactor with 70.18 grams tetraisopropyl titanate and 160 grams anhydrous toluene. The reaction mixture was heated with agitation at about 25° C for about 19 hours and then filtered. 10.2 Grams catalyst was obtained after washing and air-drying. The catalyst contained only 2.9 weight percent bound titanium even though the TPT/ support ratio was identical to that used in the preparation of the immobilized catalyst of Example I.

To evaluate the above catalyst and the immobilized catalyst, a mixed ester base stock was prepared. The mixed ester was obtained by reaction of adipic acid, 1,3-butylene glycol and 2-ethylhexanol (equivalents ratio 1.0:1.125:0.125) at a temperature of 225° C while removing water. To facilitate water removal a vacuum was applied during the latter stages of the reaction. When the acid value reached about 25, the reaction was terminated. The resulting ester product had an acid value of 25.4, 100° F viscosity of 197 centistokes and percent transmittance of 98/100. 1000 Grams of this base stock were used in the subsequent catalyst evaluations which are as follows:

1000 Grams of the ester base stock was combined with 0.01 weight percent of each catalyst and the reaction mixture heated to 225° C in a nitrogen atmosphere. A vacuum (123 mm Hg) was then applied to the system while maintaining the temperature at 225° C. When 9.5 mls water was recovered the vacuum was lowered to 0.8 mm Hg and the reaction continued for exactly 30 minutes. At this point heating was terminated and the vacuum broken with nitrogen. 1.5 Weight percent diatomaceous earth filtering aid was added when the reaction mixture had cooled to 195° C and the mixture filtered. Acid value and kinematic viscosity were obtained for the two polyester products with the following results:

|  | Example I | U.S. Pat. No. 3,817,931 |
|---|---|---|
| POLYESTER PREPARED USING CATALYST OF: | | |
| Acid Value | 0.6 | 1.4 |
| 100° F Viscosity (centistokes) | 1740 | 876 |

From the above data it is evident that appreciably more polyesterification has occurred using the immobilized catalyst of this invention. Also, it can be seen that the supported catalysts have excellent hydrolytic stability and thus do not limit the process of this invention to those esterification reactions where water is not formed as a by-product 54 Grams of each of the above catalysts were combined with 76 grams isopropyl alcohol (91%) and 135 grams water and the mixture refluxed at 84° C for 2 hours. The mixture was then filtered, and the catalyst washed with isopropanol and dried. After the above treatment the catalyst of Example I contained 38.2 weight percent bound titanium and the reference catalyst contained 2.8 weight percent bound titanium. Both catalysts (0.01 weight percent) were reevaluated for activity with the mixed ester base stock as previously described. The following results were obtained:

|  | Example I | U.S. Pat. No. 3,817,931 |
|---|---|---|
| POLYESTER PREPARED USING CATALYST OF: | | |
| Acid Value | 0.8 | 1.3 |
| 100° C Viscosity (centistokes) | 1540 | 822 |

It is readily apparent that the immobilized catalyst of this invention still had excellent activity after such water treatment. The reference catalyst activity was reduced to approximately the same activity as the untreated naturally acidic clay support which upon evaluation (using the same procedure) yielded a polyester having an acid value of 1.7 and 100° F viscosity of 802 centistokes.

EXAMPLE X

To further show the versatility of the process of this invention a series of supported catalysts wherein the tetraisopropyl titanate/support ratio was varied were prepared in the usual manner. The hydrocarbon used was mineral oil and the support was montmorillonite clay. The catalysts were as follows:

| Catalysts | TPT/Clay | % Bound Ti |
|---|---|---|
| Xa | 0.25 | 5.2 |
| Xb | 0.50 | 7.9 |
| Xc | 1.0 | 13.4 |
| Xd | 1.5 | 20.3 |

These catalysts were used to effect transesterification of the base stock of Example IX following the same procedure. The resulting polyester products had 100° F viscosity of 1030, 994, 1330 and 1440 centistokes, respectively.

EXAMPLE XI

Ninety parts alumina-silica pellets (⅛ degrees) were reacted with 45 parts tetraisopropyl titanate in white oil (70 SUS) at 200° C for 1½ hours. The washed and dried catalyst pellets (50 parts) formed a fixed catalyst bed in a reactor adapted for continuous operation. A mixed ester product obtained by reacting adipic acid, 1,3-butylene glcyol and 2-ethylhexanol, such as described in Example IX, but taken to an acid value of 2.2 (100° F viscosity of 270 centistokes) was continuously added to the reactor maintained at 225° C and 1.0 mm Hg at a rate varying between about 2–5 mls per minute while removing polyester at a comparable rate. After two hours operation the viscosity (100° F) of the product being removed reached 1300 cs. At this point, operation was continued for an additional hour and the viscosity of the polyester product being collected never dropped below 1300 centistokes. About 250 grams/hour polyester was obtained.

EXAMPLE XII

A supported vanadium catalyst was prepared by reacting 10 grams of a naturally acidic montmorillonite clay and 15 grams tributyl vanadate in 160 grams mineral oil by heating the reaction mixture with agitation from room temperature to 250° C over a period of 1¼ hours. Distillate began coming off at about 200° C and a total of 6.2 mls butanol was removed. Butene was also collected in the dry ice trap. After cooling and filtration the product was washed with isopropanol until the filtrate had only a very pale yellow coloration. The final weight of the product after air-drying was 14.8 grams. The supported catalyst contained 16.1 percent by weight vanadium. In much the same manner, an immobilized zirconium catalyst was prepared. The support used for this reaction was a synthetic silica/alumina (13% as $Al_2O_3$). The alumina/silica support (10.8 grams) was charged to a reactor with 120 grams mineral oil (70 SUS) and 10.1 grams tetrabutylzirconate. The mixture was then gradually heated to about 220° C over a period of about 3 hours while removing butanol and venting gases. After filtering, washing and air-drying 13.25 grams of a supported catalyst (7.3 weight percent zirconium) was obtained. Both these products proved to be effective esterification catalysts.

EXAMPLE XIII

Methyl oleate was prepared as follows: A reactor was charged with 500 grams oleic acid, 58 grams methanol and 5 weight percent (based on the oleic acid) of the catalyst of Example I. Heating was begun to 140° C and a water/methanol mixture began distilling at about 80° C. Subsurface addition of methanol (29 grams/hour) was begun while heating to 170° C. The reaction was terminated when the acid value of the reaction mixture reached about 1. The methyl oleate, after filtering with a diatomaceous earth filter aid, had an acid value of 0.9 and contained less than 1 ppm titanium.

EXAMPLE XIV

Polyester products were prepared using 1000 grams of the ester base stock of Example IX (% T=98/100) with (a) 0.58 grams of the supported catalyst of Example 1 and (b) 1.30 grams tetraisopropyl titanate. Both reaction systems contained 219 ppm Ti. Vacuum (160 mm Hg) was applied to each system while heating at 225° C until 9.5 mls $H_2O$ was recovered at which time the pressure was reduced to 19.6 mm Hg and the reactions continued for two hours and then terminated. About the same amount of distillate was recovered for both reactions. After filtering with 1.5 weight percent diatomaceous earth filtering aid, the polyester product (A.V. 0.5) obtained using the immobilized catalyst had a color of 95/100 whereas the polyester (A.V. 0.4) obtained using the homogeneous tetraisopropyl titanate catalyst was 60/95. It is apparent that a marked improvement in color is obtained with the process of this invention using the immobilized transition metal catalysts. Also, with the polyester prepared by method (b) the level of residual titanium was about 10 times greater than obtained by method (a).

We claim:

1. A process for the batch, continuous or semicontinuous preparation of carboxylic acid esters by direct esterification of a carboxylic acid or anhydride with an alcohol or by ester interchange of a carboxylic acid ester with another carboxylic acid ester, an alcohol or carboxylic acid which method comprises heating the reactants in a liquid state at a temperature between 100° C and 300° C in the presence of at least 0.005 weight percent, based on the reactants, of an immobilized supported transition metal catalyst containing from about 3 to 60 weight percent of a transition metal selected from Groups IVb, Vb and VIb, said transition metal being present on and bound to a support matrix by bridging oxygen linkages as a polymeric cross-linked network wherein the transition metal atoms are bonded to each other by bridging oxygen linkages.

2. The process of claim 1 wherein the catalyst is obtained by heating at a temperature in the range 100° C to 300° C a hydroxylic support with a transition metal alkoxide of the formula $$M(OR)_nQ_m$$

where M is a transition metal selected from Groups IVb, Vb and VIb, OR is an alkoxy radical containing 1 to 18 carbon atoms, n is an integer from 2 up to the valence of the metal M, Q is an inert group which will not react with the hydroxyl groups of the support, the alkoxide radical OR or alcohol ROH formed therefrom and m is an integer so that $n + m$ satisfies the valence of the metal M, in an inert liquid hydrocarbon and in the presence of water to effect condensation of the transition metal alkoxide and the reaction of the transition metal alkoxide or oligomer thereof with the surface hydroxyl groups, the ration of said transition metal alkoxide molecules per surface hydroxyl group being greater than 1:1 and up to $10^6:1$.

3. The process of claim 2 wherein the inert hydrocarbon is an aliphatic essentially saturated hydrocarbon having a boiling point greater than about 140° C, the weight ratio of the hydrocarbon to support is between about 0.5:1 and 50:1, the metal M is selected from the group consisting of titanium, zirconium, hafnium or vanadium and OR is a saturated branched or straight-chain alkoxy radical containing 2 to 8 carbon atoms.

4. The process of claim 3 wherein the reaction is conducted in the range 120°–250° C, the hydroxylic support is selected from the group consisting of silica, alumina or mixtures thereof and the ratio of transition metal alkoxide molecules per hydroxyl group available on the support is between about 1.5:1 and $10^4:1$.

5. The process of claim 4 wherein the transition metal alkoxide is a titanium tetralkoxide.

6. The process of claim 1 wherein the transition metal is selected from the group consisting of titanium, zirconium, hafnium and vanadium.

7. The process of claim 6 wherein the support is selected from the group consisting of silica, alumina and mixtures thereof and contains from about 5 to 50 weight percent bound transition metal.

8. The process of claim 7 wherein the transition metal is titanium.

9. The process of claim 7 conducted at a temperature from about 125° C to 250° C with about 0.001 to 10 weight percent of the catalyst.

10. The process of claim 9 wherein the transition metal is titanium.

11. The process of claim 10 wherein the catalyst is in the form of a finely divided powder.

12. The process of claim 9 which is conducted under reduced pressure.

* * * * *